United States Patent [19]

Poli

[11] Patent Number: 4,839,387

[45] Date of Patent: Jun. 13, 1989

[54] DERIVATIVE OF THIAZOLIDINE-4-CARBOXYLIC ACID, ITS PREPARATION AND PHARMACEUTICAL COMPOSITIONS CONTAINING IT

[75] Inventor: Stefano Poli, Quinto De Stampi-Rozzano, Italy

[73] Assignee: Poli Industria Chimica S.P.A., Milan, Italy

[21] Appl. No.: 144,528

[22] Filed: Jan. 15, 1988

[30] Foreign Application Priority Data

Jan. 26, 1987 [IT] Italy ................ 19165 A/87

[51] Int. Cl.$^4$ .................. C07K 5/06; A61K 37/02
[52] U.S. Cl. ........................... 514/19; 548/201
[58] Field of Search .................... 548/201; 514/19

[56] References Cited

U.S. PATENT DOCUMENTS 4,085,954  8/1987  Palla ........................ 71/90

Primary Examiner—Robert Gerstl
Attorney, Agent, or Firm—Bucknam and Archer

[57] ABSTRACT

3-L-pyroglutamoyl-thiazolidine-4-carboxylic acid, prepared starting from an activated ester of L-pyroglutamic acid from pyroglutamoyl chloride and L-thiazolidine-4-carboxylic acid, exhibits interesting immunostimulant, antitoxic, antiinflammatory, antioxidant and anti-aging properties.

6 Claims, No Drawings

DERIVATIVE OF THIAZOLIDINE-4-CARBOXYLIC ACID, ITS PREPARATION AND PHARMACEUTICAL COMPOSITIONS CONTAINING IT

The present invention concerns 3-L-pyroglutamyl-L-thiazolidine-4-carboxylic acid, having formula I

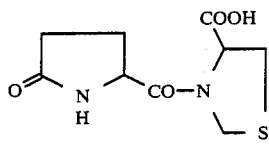

its pharmaceutically acceptable salts, a process for its preparation and pharmaceutical compositions endowed with anti-toxic, anti-oxidant, immunostimulating, antiinflammatory and anti-aging properties.

Examples of salts according to the invention are those with non-toxic and pharmaceutically acceptable bases such as lysine, arginine, alkali or earth-alkali hydroxides, tromethamine, triethylamine, triethanolamine, piperidine, etc. Some salts may be endowed with peculiar advantages such as higher solubility, better pharmacokinetic or organoleptic properties, higher stability, etc.: all these aspects are in any way subsidiary to the main physiological action of the acid I. The compound I is infact endowed with advantageous pharmacological properties such as the ability of protecting rat's liver from paracetamol intoxication, the ability of decreasing in mice the effects of exposure to ionizing radiation and the ability of positively influencing the immune system.

In the following pharmacological tests hereinafter reported, the compound I, also referred to as PGTCA, has been compared with pyroglutamic acid (PGA) and with thiazolidine-4-carboxylic acid (TCA).

EFFECTS ON PARACETAMOL INTOXICATION IN THE RAT

Male Wistar rats, mean weight of 150±10 g were used, which, after suitable housing, were subjected to the test:

(a) Test after single i.p. administration

The animals were divided in 7 groups, comprising 20 animals each, according to the following scheme:
I group: control
II group: PGTCA 4.1 μmoles/kg i.p.
III group: PGTCA 41 μmoles/kg i.p.
IV group: PGTCA 205 μmoles/kg i.p.
V group: PGA 4.1 μmoles/kg +TCA 4.1 μmoles/kg
VI group: PGA 41 μmoles/kg +TCA 41 μmoles/kg
VII group: PGA 205 umoles/kg +TCA 205 μmoles/kg.

The animals of each group, fasting since 12 hours, were treated with paracetamol at the dose of 5000 mg/kg by the oral route. The different pharmacological treatments were carried out contemporaneously with the paracetamol administration. After 48 hours from treatment, the death-rate was assessed in the various experimental groups. The liver was taken from the surviving animals, sacrificed by decapitation, and from the dead animals and an histopathologic examination was carried out.

The degree of liver impairment has been evaluated as:
degree O: normal histologic examination
degree I: centrolobular necrosis extended to less than 25% of the lobule
degree II: extended centrolobular necrosis, with lesions bridging adjacent centrolobular areas
degree III: massive necrosis.

In order to evaluate the lesion degree, 6 different sections were taken from each organ.

(b) Test after repeated i.p. administration

The same treatment schedule as in (a) was used.

The animals of groups II–VII were treated daily for 8 days. At the 8th day, contemporaneously to the various considered pharmacological treatments, the animals of the 7 groups (fasting since 12 hours) were administered with paracetamol (5000 mg/kg per os). The animals were observed for the subsequent 48 hours; the animals of groups II–VII were continuously treated as above reported.

After 48 hours from the paracetamol administration, the surviving animals were examined and the liver was subjected to the histopathologic examination.

The results, reported in the following table I, show that the acute treatment with PGTCA, both at the highest dose (205 μmoles/kg i.p.) and at the intermediate dose (41 μmoles/kg i.p.) induces a significant decrease of liver impairment by an high dose of paracetamol.

The combination PGA+TCA induces a significant decrease of the liver impairment only at the highest dose (205 μmoles/kg i.p. of PGA and TCA).

PGTCA, finally, reduces the death-rate by paracetamol both at the highest and at the intermediate dose, whereas the effect of the combination of PGA+TCA is shown only at the highest dose.

Even in the test after repeated administration the superiority of the PGTCA treatment with respect to the treatment with the combination of PGA+TCA (table II) is evident.

EFFECTS ON THE CONSEQUENCES OF THE EXPOSURE TO THE IONIZING RADIATION

Swiss male mice weighing 30±5 g, divided in 7 groups of 20 animals each, were used according to the above reported schedule.

The pharmacological treatments were carried out for 15 days before the irradiation and prosecuted up to the end of the experiment. The control animals received the vehicle alone.

At the 15th day, all the animals were irradiated (Philip Metalix ® apparatus, 180 KV, 15 mA, with Cu filter 0.5 mm +AI mm) with the administration of 700 r of x rays.

All the animals were checked daily, for 15 days after irradiation. The radio-protection degree was calculated as survival % at 10 and 15 days. The results, reported in table III, show that PGTCA has a remarkable radioprotective activity both at the highest and at the intermediate dose.

The activity of the combination PGA +TCA appears only at the highest dose.

ACTIVITY ON SOME IMMUNOLOGICAL PARAMETERS IN THE MALE RAT

In order to evaluate a possible immunostimulating or immunomodulating activity, models of physiological or paraphysiological immunodeficiency must be used. One of the most used model for this purpose is the aging. Aging, infact, is associated with a decrease of the T helper lymphocytes function and with a depression of the T-lymphocytes immunodependent responses:

delayed-type hypersensitivity, proliferative response to mitogens, differentiation of cytolytic T-cells. The mechanisms involved in this phenomenon may comprise a decreased production of thymic hormones correlated with thymic involution, induction of suppressor T-cells and impaired synthesis or utilization of interleukin.

The B cells are usually less impaired. For this reason, the effect of the in vivo PGTCA treatment of young and old animals was studied, using 2 tests indicative of the status of cellular lymphocyte reactivity.

For this purpose, male adult rats (5–6 months old) were used as animal model with normal immunocompetent system, and old rats (17–18 months) as a paraphysiological immunodeficiency model.

The PGTCA treatment has been carried out i.p. at the dose of 1, 10 or 50 mg/kg twice a day for 4 weeks. The used immunological tests were the delayed-type hypersensitivity induced by dinitrochlorobenzene (DNCB) and the T-lymphocyte response to concanavaline A (ConA).

SENSITIZATION WITH DNCB

After 4 weeks of PGTCA pre-treatment (or vehicle), 0.02 ml of DNCB (solubilized in acetone at the concentration of 200 mg/ml) was applied to each animal (5 rats per group) on the cutis of the back, on an area of about 1 $cm^2$. The subsequent inflammatory reaction was evaluated by measuring the diameter of the reddish area by means of a thickness gauge from day 1 to day 7.

During this period the animals were constantly treated.

TEST OF BLASTIZAZION WITH CONA

After 4 weeks of PGTCA treatment at the doses of 1,10 and 50 mg/kg, the animals were sacrificed and the spleen was removed in sterile conditions. The isolation of lymphocytes was obtained by an isolimph gradient. The lymphocytes were incubated in micro-walls, at the concentration of $1 \times 10^6$ cells/ml, in the presence of ConA (2.5 µg/ml), for 48 hours. The mitogen activity was evaluated by incorporation of $^3H$-thymidine for 16 hours.

From the results obtained, it is evident that the old animals show a reduction of the response to DNCB, evaluated as inflammation area. The PGTCA treatment caused a significant increase of the response only at the dose of 50 mg/kg in young animals, whereas in the old ones a maximum enhancing increase was noticed already at the dose of 10 mg/kg. The immnulostimulating activity of PGTCA was confirmed by the test of blastizazion by ConA (table IV). Also in this case the response proved to be more enhanced in the old animals presenting a certain degree of cellular immunity deficiency.

In the mouse, a cytotoxic-kind of hypersensivity reaction, evaluated in the test of T cells forming rosettes with sheep red blood cells, was used (S.D. Wilson Immunology, 1971, 21, 233).

The treatment was carried out by intraperitoneal route at the dose of 50 mg/kg twice a day, according to the methods shown in tables V A/B.

CD-I male mice weighing about 25 g are treated with PGTCA for 8 days. After 4 days from the start of the treatment the animals were immunized with $5 \times 10^8$ sheep red blood cells in 0.2 ml of PBS i.p. The rosette test was carried out 6 days after the immunization. The mice were killed and the spleen was removed and placed in ice cold Hank solution, triturated, homogenized and gauze filtered.

$6 \times 10^7$/ml of spleen cells +100 /µl of red blood cell suspension $3 \times 10^8$/µul were mixed in 0.8 ml of Hank and stirred for 1 min.

The samples were incubated for 24 h at 4° C. without stirring and then, after stirring, the number of rosette forming cells/ml was determined by the Bürker apparatus. In the rosette test, the PGTCA treatment causes a significant increase of the rosette number in comparison with the control in sensitized animals, whereas no significant change was noticed in not sensitized animals. These results allow to affirm that PGTCA is active on T lymphocyte cell population and do not increase the lymphocyte B number, showing therefore a specific immunostimulation.

TABLE 1

| Dose | Control | PGTCA | | | PGA + TCA | | |
|---|---|---|---|---|---|---|---|
| (microm/kg ip) | | 4.1 | 41 | 205 | (4.1 + 4.1) | (41 + 41) | (205 + 205) |
| n. | 20 | 20 | 20 | 20 | 20 | 20 | 20 |
| Death rate % | 90 | 85 | 75 | 60 | 90 | 85 | 75 |
| Liver impairment degree | | % distribution of liver impairment degrees | | | | | |
| 0 | 0 | 0 | 0 | 5 | 0 | 0 | 0 |
| 1 | 0 | 0 | 5 | 15 | 0 | 0 | 10 |
| 2 | 0 | 10 | 20 | 15 | 0 | 10 | 15 |
| 3 | 100 | 90 | 75 | 65 | 100 | 90 | 75 |

TABLE II

| Dose | Control | PGTCA | | | PGA + TCA | | |
|---|---|---|---|---|---|---|---|
| (microm/kg ip) | | 4.1 | 41 | 205 | (4.1 + 4.1) | (41 + 41) | (205 + 205) |
| n. | 20 | 20 | 20 | 20 | 20 | 20 | 20 |
| Death rate % | 90 | 85 | 70 | 50 | 90 | 75 | 65 |
| Liver impairment degree | | % distribution of liver impairment degrees | | | | | |
| 0 | 0 | 0 | 0 | 5 | 0 | 0 | 0 |
| 1 | 0 | 0 | 0 | 15 | 0 | 0 | 0 |
| 2 | 0 | 10 | 35 | 25 | 10 | 15 | 30 |
| 3 | 100 | 90 | 65 | 55 | 90 | 85 | 70 |

TABLE III

| Dose | Control | PGTCA | | | PGA + TCA | | |
|---|---|---|---|---|---|---|---|
| (microm/kg ip) | | 4.1 | 41 | 205 | (4.1 + 4.1) | (41 + 41) | (205 + 205) |
| n. | 20 | 20 | 20 | 20 | 20 | 20 | 20 |
| Death-rate % | | | | | | | |
| 10 gg | 20 | 20 | 15 | 10 | 20 | 20 | 20 |
| 15 gg | 55 | 45 | 20 | 15 | 50 | 45 | 35 |

TABLE IV

| PGTCA treatment | $^3H$—thymidine cpm/well | increase % | P |
|---|---|---|---|
| Adult rats (5–6 months) | | | |
| 0 | 32500 ± 1130 | — | — |
| 1 mg/kg | 31806 ± 970 | −2.1 | NS |
| 10 mg/kg | 34165 ± 540 | +5.1 | NS |
| 50 mg/kg | 35785 ± 240 | +10.1 | <0.01 |
| Old rats (17–18 months) | | | |
| 0 | 23163 ± 841 | — | — |
| 1 mg/kg | 23553 ± 923 | +1.6 | NS |
| 10 mg/kg | 26012 ± 316 | +12.3 | <0.01 |

TABLE IV-continued

| PGTCA treatment | ³H—thymidine cpm/well | increase % | P |
|---|---|---|---|
| 50 mg/kg | 27540 ± 439 | +18.9 | <0.01 |

TABLE V

| T-cells forming rosette with sheep red blood cells | | | |
|---|---|---|---|
| Groups | No. mice | No. rosette/$10^6$ spleen cells m ± E.S. | Var. % |
| Treatment: for 8 days Mice sensitized with red blood cells | | | |
| (A) Controls (NaCl 0.9% i.p.) | 10 | 7680 ± 859 | |
| PGTCA 100 mg/kg b.i.d. i.p. | 10 | 10840* ± 948 | +41 |
| Treatment: for 8 days Mice not sensitized with red blood cells | | | |
| (B) Controls (NaCl 0.9% i.p.) | 5 | 900 ± 200 | |
| PGTCA 100 mg/kg b.i.d. i.p. | 5 | 790 ± 170 | −12 |

*p < 0.05

Compound I is also active, at the dose of 10 mg/kg and even more at 50 mg/kg, in improving the neuro-cerebral performances in the old rat. A similarly favourable influence was noticed on the sexual behaviour of the male rat, with reduction of latencies and increase of the frequences of sexual acts.

For the considered therapeutic use, the compound I is suitably formulated into pharmaceutical compositions using usual methods and excipients, such as those described in "Remington's Pharmaceutical Sciences Handbook", Hack Publ. Co. N.Y. USA.

Examples of said pharmaceutical compositions comprise tablets, capsules, sugar-coated tablets, granulates or solutions for oral or parenteral use.

Typically, a unit dose will contain from 10 to 500 mg of active principle. The daily dose will depend on the patient's condition and on the seriousness of the pathology: it will be usually ranging from 0.1 to 4 g daily, in 2 or 3 administrations by the oral route, whereas by parenteral administration 50 to 2000 mg per day will generally suffice.

The present invention concerns also a process for the preparation of the compound of formula I, characterized by reacting an activated ester of pyroglutamic acid with L-thiazolidine-4-carboxylic acid in the presence of an organic base such as triethylamine, diethylisopropylamine or higher trialkylamine in solvents such as DMF, aliphatic dialkylamides or DMSO.

As an activated ester, the ester with pentachlorophenol, 2,4,5-trichlorophenol, N-hydroxysuccinimide or L-thiazolidine-4-carboxylic acid in an alkaline solution with L-pyroglutamoyl chloride, may be used.

The structure of the product has been confirmed by elemental analysis (C,H,N,S) and from the NMR and IR spectra.

The following non limitative examples illustrate the invention.

EXAMPLE 1

60 g (0.158 mol.) of pentachlorophenyl-L-pyroglutamate, prepared as described in J. Med. Chem. 13, 844 (1970), 20.85 g (0.158 mol.) of 4-thiazolidine carboxylic acid and 16 g (0.158 mol.) of triethylamine in 450 ml of dimethylformamide were stirred for 24 h at room temperature.

After filtration and solvent evaporation at reduced pressure and at a temperature lower than 15° C., the residue was treated with water, the pentachlorophenol extracted with ethyl eter, the aqueous phase was acidified with hydrochloric acid and the precipitate formed was filtered at 10° C., which was crystallized from water obtaining a white crystalline product melting at 192–194° C. (70% yield).

Analysis for $C_9H_{12}N_2O_4S$:

| | C % | H % | N % | S % |
|---|---|---|---|---|
| Calc. | 44.25 | 4.95 | 11.46 | 13.12 |
| Found | 44.35 | 4.89 | 11.50 | 13.16 |

$^1$H—NMR (DMSO/TMS int.)

| δ | | |
|---|---|---|
| 2.15 | (m, 4H) | —CH$_2$—CH$_2$— |
| 3.25–3.35 | (m, 2H) | —S—C$\underline{H}_2$—CH— |
| 4.35–4.5 | (s, 2H) | —N—C$\underline{H}_2$—S— |
| 4.55 | (m, 1H) | —NH—C$\underline{H}$— |
| 4.88 | (m, 1H) | —C$\underline{H}$—COOH |
| 7.8 | (s, 1H) | —NH— ⎫ exchange |
| 13 | (br, 1H) | —COOH ⎭ with D$_2$O |

IR (K Br)
ν (cm$^{-1}$)
3300 (NH)
1710 (CO—NH)
1680–1620 (COOH; N—C = 0)
$[\alpha]_D^{25}$ −150° (C2 in HCl 5N)

EXAMPLE 2

2N NaOH and a solution of 14.8 g (0.1 mol.) of L-pyroglutamoylchloride (US 4 278 681) in 25 ml of acetone were added simultaneously to a stirred solution of 13.3 g (0.1 mol.) of L-thiazolidine-4-carboxylic acid in 50 cc of 2N NaOH keeping the temperature at 0° C. and the pH from 7.5 to 8.5.

When the addition was over, the mixture was concentrated to half volume under reduced pressure, acidified with conc. HCl, the formed crystals were filtered after standing at 0° C. and re-crystallized from water, obtaining 12 g (49%) of a product having the same characteristics of Example 1.

I claim:

1. 3-L-pyroglutamyl-L-thiazolidine-4-carboxylic acid of formula I

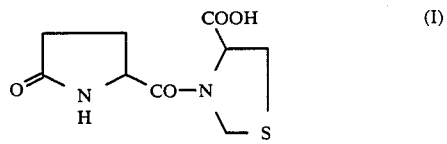

and its pharmaceutically acceptable salts.

2. A pharmaceutical composition capable of stimulating the immune system, protecting from paracetamol intoxication protecting from ionizing radiation and having antiinflammatory, antioxidant and anti-aging properties, which contains as the active principle 3-L-pyroglutamyl-L-thiazolidine-4-carboxylic acid of formula I

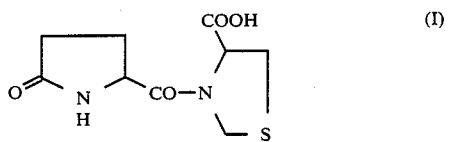

or a pharmaceutically acceptable salt thereof in admixture with a pharmaceutically acceptable vehicle.

3. The composition according to claim 2 in form of tablets, capsules, sugar-coated tablets, granules or solutions for parenteral or oral administration containing 10–500 mgs of said compound of formula I per unit dose.

4. The method of protecting a living subject from ionizing radiation, paracetamol intoxication and providing anti-oxidant, immunostimulating, antiinflammatory, anti-aging properties, which consists of administering to said subject by the oral or parenteral route, a composition containing as the active principle the compound of formula I 3-L-pyroglutamyl-L-thiazolidine-4-carboxylic acid of formula I

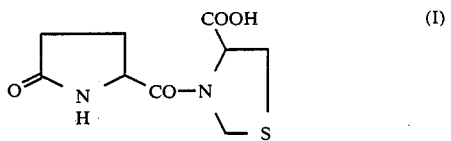

or a pharmaceutically acceptable salt thereof, the total dose of said compound of formula I being 0.1–4 g. daily.

5. The method according to claim 4 where said composition is administered 2–3 times daily.

6. The method according to claim 4 wherein said composition is administered parenterally once daily.

* * * * *